United States Patent [19]

Wilkes

[11] 3,976,703
[45] Aug. 24, 1976

[54] HYDROFORMYLATION USING ARYL SULFONATE STABILIZER FOR COBALT CATALYST

[75] Inventor: John B. Wilkes, Richmond, Calif.

[73] Assignee: Chevron Research Company, San Francisco, Calif.

[22] Filed: Apr. 4, 1974

[21] Appl. No.: 457,746

Related U.S. Application Data

[63] Continuation-in-part of Ser. No. 32,386, April 27, 1970, abandoned.

[52] U.S. Cl. .......................... 260/632 HF; 260/598; 260/604 HF; 260/617 HF; 260/631 R; 260/631.5
[51] Int. Cl.$^2$.................. C07C 27/20; C07C 29/16
[58] Field of Search .............. 260/632 HF, 604 HF, 260/598, 631 R, 631.5, 617 HF

[56] References Cited
UNITED STATES PATENTS
2,695,315  11/1954  Parker .......................... 260/604 HF FOREIGN PATENTS OR APPLICATIONS
530,889  9/1956  Canada ......................... 260/604 HF OTHER PUBLICATIONS
Hath, "Higher Oxo Alcohols", 1957, pp. 13–19.

Primary Examiner—Joseph E. Evans
Attorney, Agent, or Firm—G. F. Magdeburger; John Stoner, Jr.; T. G. DeJonghe

[57] ABSTRACT

The destructive dissociation of a cobalt carbonyl complex compound in the liquid phase is inhibited by the presence of an aryl sulfonate stabilizer.

5 Claims, No Drawings

HYDROFORMYLATION USING ARYL SULFONATE STABILIZER FOR COBALT CATALYST

CROSS-REFERENCE TO RELATED APPLICATION

This application is a continuation-in-part of U.S. application Ser. No. 32,386, filed Apr. 27, 1970 now abandoned.

FIELD OF INVENTION

This invention relates to a method for the stabilization of a cobalt carbonyl complex compound in the liquid phase. More particularly, it relates to a method for the stabilization of cobalt carbonyl complex compounds in a hydroformylation reaction system effected by the action of an aryl sulfonate inhibitor. Still more particularly, this invention relates to the use of alkyl aryl sulfonate compounds as catalyst stabilizers in the production of alcohols and/or aldehydes from olefinically unsaturated organic compounds by the cobalt carbonyl catalyzed addition reaction of carbon monoxide and hydrogen to the carbon-to-carbon linkage(s) of these unsaturated compounds.

BACKGROUND OF INVENTION

Cobalt carbonyl compounds including dicobalt octacarbonyl, cobalt hydrocarbonyl etc. as such or in modified forms are known for their use as catalysts for a variety of reactions relating to olefinic unsaturated organic compounds including the hydroformylation (oxonation) of olefins, isomerization of olefins, carbonylation of amines and aromatic nitriles, hydrosilation of olefins and the like. These catalyst complexes are subject to serious limitations in that unless carbon monoxide pressures in excess of cobalt carbonyl complex equilibrium values are maintained in their presence, a destructive dissociation into cobalt metal and residue occurs under reaction conditions. Catalytic activity is thus lost and cobalt metal is plated-out on reactor walls and associated transfer piping. From time to time the accumulated metal must be removed by a suitable means, usually by the use of aqueous nitric acid or a similar undesirably corrosive and inconvenient agent.

THE INVENTION

It has now been found that aryl sulfonate solutes inhibit the destructive dissociation of cobalt carbonyl complex compounds in the liquid phase. The liquid phase is a one phase or homogeneous system. It has also been found that an aryl sulfonate solute inhibits the formation of cobalt metal plates on the sides of the system in contact with the contained solution. In addition, the presence of at least a minor amount, e.g., 0.001 mol per mol of cobalt in the complex compound of an alkyl aryl sulfonate in a hydroformylation reaction mixture stabilizes the cobalt carbonyl complex compound comprising the hydroformylation catalyst by inhibiting the destructive dissociation ordinarily experienced by these catalysts in the hydroformylation of unsaturated organic compounds under hydroformylation reaction conditions. Aryl sulfonates of the formula $R_nYSO_3M$ in which R is an unsubstituted alkyl group having a carbon atom content in the range from about 3 to 30, in which Y is an aryl aromatic carbocyclic nucleus having a carbon atom content in the range from 6 to about 13, in which M is a cation of the group ammonium, calcium and the alkali metals, in which $n$ is an integer in the range from 1 to about 4, inclusive, and in which the R groups where $n$ is greater than 1 may be the same or different, are useful for the stabilization of cobalt carbonyl complex compounds in the hydroformylation of unsaturated organic compounds.

In addition to the aforedescribed advantages which obtain from the use of an aryl sulfonate in conjunction with a cobalt carbonyl complex compound in the liquid phase, surprisingly, the presence of these inhibitors permits the employment of carbon monoxide pressures well below conventional equilibrium pressures for cobalt carbonyl complex compounds in hydroformylation reaction systems where the sulfonate is the sole non-gaseous stabilizer present.

In a preferred embodiment of 1-alkene, for example 1-octene, cobalt octanoate, and the sodium salt of a straight chain $C_{15}$–$C_{20}$ alkylbenzene sulfonate are charged to a pressure reactor, an autoclave, in a mol ratio of 1:0.0015:0.00015, respectively. Hydrogen and carbon monoxide gas are charged to the sealed autoclave in the mol ratio 2:1, respectively, and the reactor and charge is maintained at a temperature of about 175°–180°C. and a total system pressure of about 1800–2000 psig for a period of about 2 hours. The resulting product mixture contains, based upon the olefin feed, about 90–95 weight percent of nonyl alcohol, a trace of nonyl aldehyde, about 8–9 weight percent of alkane and about 25 weight percent of high molecular weight by-product (called thick oil in the oxonation art). Little or no cobalt metal is found to be deposited upon the walls of the reactor and most of the cobalt charged is present in the product mixture as $Co_2(CO)_8$.

The hydroformylation of unsaturated organic compounds catalyzed by cobalt carbonyl complex compounds using carbon monoxide and hydrogen (i.e., the classic unmodified oxo-reaction system) is well known in the art. The addition of the aryl sulfonates of the present invention to the unmodified hydroformylation reaction systems of this prior art is in general beneficial and is contemplated herein including the reaction conditions, catalysts and reactants.

Briefly, hydroformylation reactions may be illustrated by the general equation:

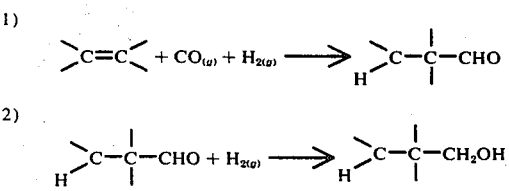

wherein the unsatisfied valence bonds are attachments to the atoms or radicals necessary to complete the olefinic compound. Substantial partial pressures of carbon monoxide and hydrogen are required for the reaction to proceed with suitable relative proportions of hydrogen to carbon monoxide being in the range 0.5–10 to 1 respectively, and preferably 1–3 to 1. Normally in the absence of a suitable catalyst stabilization means, satisfactory total pressures (carbon monoxide plus hydrogen) are in the range 700 to 10,000 psig with corresponding temperatures being in the range 140°C. to 250°C. The present aryl sulfonate stabilizers permit satisfactory operation at system pressures in the range from about 50 psig to up to about 4000–5000 psig with the corresponding temperatures being about 75°C. to 225°C., preferably 125°C. to 200°C.

By a hydroformylation reactor, as used herein, is meant a pressure reactor, autoclave and the like, as known in the art.

In the absence of a suitable stabilization means cobalt carbonyl complex compounds equilibrate into a system which contains many members, including dicobalt octacarbonyl, cobalt hydrocarbonyl, the salt $Co[Co(CO)_4]_2$, etc. Any and all of these complex compounds are either useful hydroformylation catalysts per se or are catalyst precursors. Cobalt metal may also be a member of the above noted equilibrium set. However, in hydroformylation reactions for all practical purposes the formation of cobalt metal is an irreversible reaction and one to be avoided. Usually it is more convenient to prepare the catalyst in situ by the reaction of a cobalt oxide, a cobalt salt or soap with hydrogen and carbon monoxide in the vessel contemplated for use in a hydroformylation reaction.

The medium for the in situ preparation in general comprises a liquid reactant, for example an unsaturated organic compound or an olefinic hydrocarbon, from a reaction system for which the cobalt carbonyl complex is to serve as a catalyst. Inert liquid media or diluents such as saturated hydrocarbons, aromatic hydrocarbons, alcohols, high-boiling reaction by-products, etc., as known in the art, may also be employed.

In general, best results in terms of stabilization effects obtain when the stabilizers of the present invention are present initially, although good results are also experienced from a subsequent addition. Preferably one or more of the subject compounds are the sole stabilization means other than carbon monoxide in the reaction system.

In the active form, the stabilized cobalt carbonyl catalyst will contain most of the cobalt component in a reduced valence state, usually zero or possibly even a −1 valence.

As used herein, the term "complex compound" relates to combinations of two or more atoms, ions, or molecules which arise as a result of the formation of a bond(s) by the sharing of a pair(s) of electrons originally associated with only one of the components, and the complex possesses identifiable physical or chemical characteristics of a distinct species.

Aryl sulfonate solutes in general appear to be beneficial in the stabilization of cobalt carbonyl complex compounds where the cation is ammonium, an organic nitrogen base, an alkali metal, alkaline earth metal, or mixtures thereof. Aryl sulfonates of the formula $R_nY-SO_3M$, and molecular mixtures thereof, as defined above, are preferred for use herein, in particular where $n$ is 1 and the carbon atom content of the alkyl hydrocarbon radical portion of the sulfonate is in the range from about 12 to 30, where Y is a benzene nucleus and where M is an alkali metal cation.

Representative satisfactory carbocyclic nuclei for the above formula include benzene, naphthalene, biphenyl and the like aromatic rings. Benzene and naphthalene sulfonates are preferred.

Satisfactory alkyl radicals, R, for the above formula have a carbon atom content in the range from 3 to about 30 and representative radicals include s-octyl, n-octyl, t-butyl, i-propyl, n-propyl, s-tetracontyl, s-(2-methyl)-octyl, t-(3-ethyl)-nonyl, s-dodecyl, s-eicosanyl, s-nonadecanyl, n-hexyl, s-heptyl, s-decyl, t-(3-methyl)-tetradecyl, s-octacosanyl, s-triacontanyl, n-nonacosanyl, and the like alkyl hydrocarbon radicals. Straight chain alkyl hydrocarbon radicals are preferred.

Representative cations, M, for the above formula include lithium, sodium, potassium, calcium, and nitrogen containing ions of the formula $R_4N^{(+)}$ wherein the groups R are the same or different and may be hydrogen, or an alkyl hydrocarbon radical having a carbon atom content in the range from 1 to about 20, such as ammonium, $CH_3NH_3^{(+)}$, $(CH_3)_4N^{(+)}$, $C_6H_5CH_2NH_3^{(+)}$, $n-C_6H_{13}NH_3^{(+)}$, $(i-C_3H_7)_2NH_2^{(+)}$, $n-C_{20}H_{41}NH_3^{(+)}$, and the like cations. Sodium is preferred.

Representative inhibitors/stabilizers useful in the invention include the sodium, ammonium, lithium and calcium salts of the aryl sulfonic acids s-hexadecyl benzenesulfonic, di-s-octyl benzenesulfonic, tri-isopropyl naphthalenesulfonic, 4-s-octadecyl biphenylsulfonic, n-decyl benzenesulfonic, s-octyl, s-dodecyl benzenesulfonic, s-eicosanyl benzenesulfonic, tri-s-octyl benzenesulfonic, s-nonadecyl naphthalenesulfonic, s-octyl, s-dodecyl naphthalene sulfonic, s-hexadecyl, s-pentadecyl benzenesulfonic, s-butyl, s-tetradecyl benzenesulfonic, and the like acids.

The relative amount of the stabilizer which should be employed varies, depending upon the particular reaction conditions being employed. At the lower reaction temperatures a relatively smaller amount is satisfactory. Similarly, for a given reaction temperature as the carbon monoxide partial pressure is increased, a relatively smaller amount of the aryl sulfonate is required for satisfactory stabilization. In general, the amount of the agent used will be in the range from about 0.001 to 0.5 mol per mol of cobalt in the reaction mixture. A larger relative amount may be used, for example as much as 1–2 mols of the sulfonate per mol of cobalt, but usually no particular advantage results from the use of the larger relative amount. Usually better results obtain when the ratio is substantially less than stoichiometric, i.e., in the range from about 0.1–0.25 to 1, respectively.

The amount of catalyst desirably employed in the present process corresponds to prior art requirements. Usually catalyst concentrations, based upon the olefinically unsaturated feed (weight percentages) and calculated as cobalt metal in the range 0.05 to 5.0 weight percent are satisfactory. Preferred amounts are in the range 0.1 to 0.5.

Olefinically unsaturated organic compounds as known in the hydroformylation (oxo) art are, in general, satisfactory feeds for use in the present invention. Preferred feeds are monoolefinic hydrocarbons. Of these, linear olefins of the $C_3$ to $C_{20}$ range, propylene oligomers and the like, are the most desirable feeds. Where branched chain olefins are used for the production of oxo-alcohols, it is often more advantageous to effect the carbon monoxide-hydrogen addition to the olefinic double bond at about 140°–170°C. and to subsequently heat the reaction mixture to a higher temperature (180°–210°C.) where the reduction of the aldehyde group proceeds more favorably.

Representative olefinic hydrocarbons suitable for use herein include ethene, propene, 1-hexene, cyclohexene, beta-pinene, alpha-pinene, 2-heptene, 3-ethylpentene-1, 2-methylpentene-2, cyclopentene, di-isobutylene, propylene trimer, codimer heptenes, vinylcyclohexene, cyclododecene, 3-eicosene, 1-dodecene and the like olefinic hydrocarbons.

COBALT CARBONYL STABILITY TEST

The stabilizing action of the inhibitors of the present invention upon complex cobalt carbonyl compounds is shown by means of a suitable test. The relative stabilizing action is shown by comparative examples subjecting them to a standard set of conditions with and without the added aryl sulfonate. These conditions include:

| | |
|---|---|
| Temperature, °C. | 190 |
| Time, hrs. | 6 |
| Solvent | Mixed alcohol—alkane[(1)] |
| $H_2$:CO mol ratio | 2:1 |
| Pressure, psig | 1600–1800 |

[(1)]All runs with 0.236 grams of cobalt as octanoate in 50 g n-heptane and 50 g $C_{12-15}$ oxo alcohol.

The test is carried out in a stainless steel rocking autoclave having a glass liner. Under these conditions cobalt salts such as cobalt 2-ethylhexanoate are rapidly converted to complex cobalt carbonyls. Therefore, as a matter of convenience, the salt rather than the carbonyl compound is charged to the autoclave. After the six hours at temperature with agitation, the autoclave and contents is cooled to room temperature and vented. The solution is then filtered and analyzed for cobalt carbonyl by infrared absorption at 2041 $cm^{-1}$. Metallic solid if present and its form is noted. In the absence of stabilizers and under the foregoing conditions all of the cobalt carbonyl is converted to a cobalt metal plate which is found adhering to the walls of the glass liner and autoclave. In the presence of an effective stabilizer, little or no metal plating-out occurs, or but small amounts of filterable metal powder are formed. With stabilizers of intermediate effectiveness, little or no metal is found in the liner; but metal is found outside the liner, either deposited on the external liner wall or the autoclave wall, or loosely lodged between the liner and the autoclave wall. Decompositions outside the liner appear to be due to the higher temperatures which exist at the autoclave wall because of the proximity of the heating element and the low level of the stabilizer. The stabilizer inhibits decomposition of the cobalt carbonyl in the solution inside the liner, but does not prevent some diffusion through the vent holes in the liner into the void between the liner and the autoclave inner wall. In Table I below is listed a number of representative test results.

TABLE I

ARYL SULFONATE STABILIZERS FOR HYDROFORMYLATION SYSTEMS

| | Stabilizer | | | | Cobalt as $Co_2(CO)_n$, | |
|---|---|---|---|---|---|---|
| No. | Type | Wt.% of[(a)] Solution | Moles Per Mole Co. | Pressure[(b)] Psig | % of Cobalt Fed | Observations |
| 1 | None | — | — | 1650 | 0 | Metal plate on liner walls. |
| 2 | Pyridine | 0.16 | 0.50 | 1700 | 0 | Metal plate on liner walls. |
| 3 | $RC_6H_4SO_3Na^{(1)}$ | 0.12 | | 1750–1850 | 71 | Clean, no metal plate. |
| 4 | $(R'RC_6H_3SO_3)_2Ca^{(2)}$ | 0.09 | | " | 64, 38 | Some metal plate on 38% run. |
| 5 | $R_2C_6H_3SO_3Na^{(3)}$ | 0.12 | | " | 61 | Clean, no metal plate. |
| 6 | $(RR'C_6H_3SO_3)_2Ca^{(4)}$ | 0.1 | | " | 23 | " |
| 7 | $RC_6H_4SO_3Na^{(5)}$ | 0.12 | | " | 58 | " |
| 8 | $RC_6H_4SO_3Na^{(6)}$ | 0.12 | | " | 11 | Some metal plate noted |
| 9 | $i-(C_3H_7)_3C_{10}H_4SO_3Na$ | 0.1 | | " | 6 | Very finely divided metal dispersion. |

[(a)]All runs with 0.236 grams of cobalt as octanoate in 50 g n-heptane + 50 g $C_{12}$–$C_{15}$ oxo alcohol.
[(b)]2:1, $H_2$:CO
(1) R is $C_{15}$–$C_{18}$ linear alkyl
(2) R is $C_6$–$C_8$ linear alkyl R' is $C_{15}$–$C_{20}$ linear alkyl
(3) R is $C_8$ linear alkyl
(4) R is $C_4$–$C_9$ branched alkyl R' is $C_{15}$–$C_{20}$ linear alkyl
(5) R is $C_{18}$ linear alkyl
(6) R is $C_{15}$–$C_{18}$ polypropyl alkyl The above comparative examples illustrate that alkyl aryl sulfonates are effective stabilizers for cobalt carbonyl complex compounds. In similar tests where the cation is Li, $NH_4$, K, $C_6H_5CH_2NH_3^{(+)}$, and the like, similar stabilization effects are notable.

EXAMPLES 10–13

Advantages of the instant stabilization method are illustrated by comparative examples in which a representative feed, 1-octene, is converted to oxo alcohols in a cobalt carbonyl catalyst hydroformylation using commercial catalyst requirements, e.g., 0.2–0.5 weight percent of cobalt based upon olefin and other conditions, as noted in Table II below.

TABLE II

HYDROFORMYLATIONS WITH ARYL SULFONATE ADDITIVES

| | Cobalt | | Additive | | | Solvent | | Olefin | |
|---|---|---|---|---|---|---|---|---|---|
| No. | Source | Wt. % of Olefin | Type | Grams | Moles Per Mole Co | Type | g | Type | Grams |
| 10 | Co-octanoate | 0.25 | di-"linear" $C_7$–$C_8$ alkylbenzene Na sulfonate | 0.12 | 0.10 | None | — | 1-octene | 75 |
| 11 | Co-octanoate | 0.25 | "linear" $C_{15}$–$C_{18}$ alkyl | 1.3 | 1.0 | None | — | 1-octene | 75 |

TABLE II-continued
HYDROFORMYLATIONS WITH ARYL SULFONATE ADDITIVES

| 12 | Co-octanoate | 0.25 | benzene Na sulfonate tri-isopropyl-naphthalene-Na-sulfonate | 0.1 | 0.12 | None | — | 1-octene | 75 |
| --- | --- | --- | --- | --- | --- | --- | --- | --- | --- |
| 13 | pre-activated[(a)] co-octanoate | 0.19 | tri-isopropyl-naphthalene-Na-sulfonate | 0.05 | 0.08 | n-heptane | 50 | 1-octene | 50 |

| | Reaction Conditions | | | | Products Wt. % of Olefin | | | |
| --- | --- | --- | --- | --- | --- | --- | --- | --- |
| No. | Temp °C. | H₂:CD Mole Ratio | Press Psig | Time, Min. | Alcohol | Alde-hyde | Hydro-carbons | Thick Oil |
| 10 | 165 | 1.2:1 | 1300 | 60 | | | | |
| | 195 | 3:1 | 1800 | 60 | 100 | Trace | 2.6 | 25 |
| 11 | 177 | 2:1 | 1900 | 120 | 91 | Trace | 8.8 | 25 |
| 12 | 177 | 2:1 | 1900 | 90 | 48 | 7 | 18 | — |
| 13 | 177 | 2:1 | 1800 | 60 | 52 | 22 | 9½ | — |

[(a)]Catalyst pre-activated by reacting 90 min. at 190°C., 2:1 H₂:CO, 1800 psig, in solvent without olefin: cool to 65°C., add olefin.
(Runs 12 and 13 gave apparent low yield due to acetal formation. Needed more time, or higher temp.)

In the above hydroformylation examples the walls of the reactor were visually checked for the presence of a cobalt metal plate. None was notable.

These examples illustrate that alkyl substituted aryl sulfonates are effective stabilizers for cobalt carbonyl complex compounds under hydroformylation reaction conditions.

EXAMPLES 14–15

The following examples illustrate the hydroformylation of a 1-alkene feed, a $C_{13}$–$C_{14}$ α-olefin mixture, under conventional unmodified conditions using 0.2–0.5 weight percent of cobalt based upon the olefin and the balance of the conditions and with the results as in Table III below.

TABLE III

| CONVENTIONAL HYDROFORMYLATION SYSTEM | | |
| --- | --- | --- |
| EXAMPLE | 14 | 15 |
| HYDROFORMYLATION CONDITIONS | | |
| Temp., °C. | 175 | 200 |
| Pressure, Psig | 3500 | 4400 |
| Carbon Monoxide | 1550 | 3000 |
| Hydrogen | 1850 | 1400 |
| Time, Min. | — | 180 |
| HYDROGENATION CONDITIONS | | NOT NEEDED |
| Temp., °C. | 140 | — |
| Pressure, Psig | 1400 | — |
| YIELDS, WT.% OF FEED OLEFIN | | |
| Alcohol | 82 | 85 |
| Paraffin | 8 | 12 |
| Thick Oil | 16 | 10 |

From a comparison of Examples 14 and 15 with Examples 9–13, it is evident that alkyl aryl sulfonates stabilize complex cobalt carbonyl compounds, thereby permitting the use of lower system pressures in the hydroformylation of hydroformylatable unsaturated organic compounds.

It will be readily appreciated from the foregoing disclosure and examples that variations can be made by those skilled in the art without departing from the scope and spirit of the appended claims.

I claim:

1. In the hydroformylation of an olefinically unsaturated hydrocarbon compound of 3 to 20 carbon atoms by the addition of carbon monoxide and hydrogen to a carbon-carbon double bond of the hydrocarbon compound in a liquid phase reaction mixture wherein the reaction is catalyzed by a catalyst comprising dicobalt octacarbonyl in an inert one-phase organic liquid medium, the improvement which comprises stabilizing the catalyst by adding to the mixture an aryl sulfonate of the formula $$R_nYSO_3M$$

wherein Y is aryl of 6 to 13 carbon atoms, wherein R is an alkyl group having a carbon atom content in the range from about 3 to 30, wherein M is selected from the group consisting of alkali metal, calcium, and ammonium cations, said ammonium ions being of the formula $R_4N^{(+)}$ wherein the groups R' are the same or different and may be hydrogen, or alkyl radicals having a carbon atom content in the range from 1 to about 20, and wherein n is an integer in the range from 1 to 4, inclusive, and where n is greater than 1, said R may be the same or different groups, and wherein the hydroformylation is carried out at a pressure between about 50 and 5,000 psig and a temperature between about 75° and 225°C.

2. The hydroformylation as in claim 1 further characterized in that the stabilizer is a sodium monoalkyl benzene sulfonate in which the alkyl group has a carbon atom content in the range from about 12 to 30.

3. The hydroformylation as in claim 2 further characterized in that said alkyl group of the sulfonate is a straight chain radical.

4. The hydroformylation as in claim 1 further characterized in that for each mol of cobalt in the reaction mixture an amount of the aryl sulfonate in the range from about 0.001 to 2 mols is present in the mixture.

5. The hydroformylation as in claim 1 further characterized in that for each mol of cobalt in the reaction mixture an amount of the aryl sulfonate in the range from about 0.001 to 0.5 mol is present in the mixture.

* * * * *